United States Patent [19]
Brown

[11] Patent Number: 5,285,992
[45] Date of Patent: Feb. 15, 1994

[54] ADJUSTABLE STEP STOOL

[76] Inventor: Ronald G. Brown, Rte. 1, Box 554A, Mullins, S.C. 29574

[21] Appl. No.: 913,035

[22] Filed: Jul. 14, 1992

[51] Int. Cl.⁵ ............................................. F16M 13/00
[52] U.S. Cl. .................................... 248/421; 108/147; 297/423.45
[58] Field of Search ............... 248/421, 157, 161, 149; 182/223, 141; 297/439; 108/147; 254/122

[56] References Cited

U.S. PATENT DOCUMENTS

| | | | |
|---|---|---|---|
| 797,077 | 8/1905 | Shaw | 248/421 |
| 1,762,046 | 6/1930 | Blumenberg | 248/421 |
| 1,807,960 | 6/1931 | Brownell | 248/421 |
| 1,941,301 | 12/1933 | Hanson et al. | 248/421 X |
| 3,024,783 | 3/1962 | O'Toole et al. | |
| 3,447,635 | 6/1969 | Carlbom | 182/141 |
| 3,472,183 | 10/1969 | Goodman | |
| 3,700,070 | 10/1972 | King | 183/141 X |
| 3,917,211 | 11/1975 | Daunderer et al. | 248/421 |
| 3,982,718 | 9/1976 | Folkenroth et al. | 248/421 |
| 4,232,901 | 1/1980 | Harrington et al. | 108/147 X |
| 4,858,482 | 8/1989 | Knudsen | 248/421 X |
| 4,890,692 | 1/1990 | Oakman | 182/141 |
| 4,934,647 | 6/1990 | Edwards | 248/371 |
| 5,056,626 | 10/1991 | Mayr | 182/141 X |
| 5,145,029 | 9/1992 | Blasdell, Jr. et al. | 182/141 X |

OTHER PUBLICATIONS

Air-Lift Publication, Dec. 1972.

Primary Examiner—Ramon O. Ramirez
Attorney, Agent, or Firm—Richard C. Litman

[57] ABSTRACT

The present invention is an adjustable step stool. The step stool comprises a telescopic body which vertically expands and contracts through the actuation of a scissor assembly disposed therein. The scissor assembly includes a plurality of knee brackets pivotally joining a pair of cross bars and screw blocks. A threaded actuating rod is journaled through one screw block and is threaded through the other screw block. As the rod is rotated, the screw blocks either converge or diverge from one another acting on the knee brackets which, in turn, cause the cross bars to raise or lower, respectively. The rod is driven by an electric motor. The motor is made operable to raise and lower the step stool through the control of a pair of switches. For hands-free, relatively effortless control of the step stool, the switches are disposed beneath yet accessible through an anti-slip mat positioned on the upper surface of the top section. In the event that the motor fails to operate, that is, fails to actuate the rod, the step stool is provided with a hand crank which permits a user to raise and lower the step stool manually. Handles are provided to assist in the transportation of the stool. Anti-skid feet are employed to reduce the risk of the stool moving inadvertently.

18 Claims, 2 Drawing Sheets

ADJUSTABLE STEP STOOL

BACKGROUND OF THE INVENTION

1. FIELD OF THE INVENTION

The present invention relates to an adjustable stool and, more specifically, to an adjustable stool where the height of the stool can be varied by using foot switches mounted on the top surface of the device, allowing the hands of the user to be free to pursue the current work being engaged therein.

2. DESCRIPTION OF THE PRIOR ART

In a number of fields it is desirable, for both comfort and utility, to be able to adjust the height at which one is standing. For example, doctors and other operating room personnel, during a long procedure, may wish to change their positional attitude with respect to the patient. Extended periods of bending can lead to unnecessary fatigue and/or discomfort that, in the interest of safety and occupational satisfaction, should be minimized. The medical community is not, of course, the only fraternity with this problem. Any field where the work is, by necessity or custom, performed in a standing posture confronts this hazard. Bending over, even slightly, for protracted periods of time without relief can lead to chronic back problems, or exacerbate an already existing condition.

U.S. Pat. No. 3,472,183 issued on Oct. 14, 1969 to Robert Goodman addresses this issue and discloses a vertically adjustable table wherein a motor means controlled by a switch drives an internally threaded jack screw cylinder allowing the table to be adjusted in small increments.

U.S. Pat. No. 4,232,901 issued on Nov. 11, 1980 to Elaine M. Harrington et al. discloses an adjustable ottoman where a remotely located switch engages an electric drive system to turn a pair of chains, which, for their part, are attached to two threaded rods. By means of two sets of bars fixed to a lazy tongs arrangement, the ottoman is adjustable in respect to a vertical plane.

U.S. Pat. No. 3,982,718 issued on Sep. 28, 1976 to Richard P. Folkenroth et al. discloses an operatory chair that, using a pair of lazy tong assemblies and a threaded rod adjacent to the base of the device, can be adjusted as to height.

U.S. Pat. No. 3,024,738 issued on Mar. 13, 1962 to Phil J. O'Toole et al. discloses a mobile, collapsible display device. The device has a wheeled base, a number of telescoping sections, and is raised or lowered by a piston extending from a cylinder that is attached to a pair of pivoted levers. There are a pair of X-frame stabilizers on either side of the device, and the top is equipped with a turntable to facilitate the display of an automobile or the like.

U.S. Pat. No. 3,700,070 issued on Oct. 24, 1972 to John Calaby King discloses a scissors-type linkage where, when the linkage is in the fully collapsed position, the pivot point is above the line of action of a horizontally positioned hydraulic cylinder, overcoming the problem of a high initial force requirement.

U.S. Pat. No. 4,858,482 issued on Aug. 22, 1989 to Erik Knudsen and U.S. Pat. No. 4,934,647 issued on Jun. 19, 1990 to James S. Edwards both show scissor-type mechanisms for lift tables or universal mounts, respectively.

None of the above inventions and patents, taken either singly or in combination, is seen to describe the instant invention as claimed.

SUMMARY OF THE INVENTION

The present invention is an adjustable step stool. The step stool comprises a telescopic body having a top section, a intermediate section, and a bottom section. The telescopic body vertically expands and contracts through the actuation of inner structural elements. The inner structural elements include a scissor assembly comprising front and rear, longitudinally extending cross bars joined at a pivot point; left and right, laterally extending screw blocks; knee brackets adjoining the cross bars and the screw blocks; and a threaded actuating rod communicating with the screw blocks. As the rod is rotated, the screw blocks either converge or diverge from one another acting on the knee brackets which, in turn, cause the cross bars to rotate about their pivot points. The right side of each cross bar engages with a roller assembly which permits longitudinal movement of the cross bars. The left side of each cross bar is pivotally connected to a fixed pivot point. It is the engagement of the cross bars with the roller assemblies and the fixed blocks as well as the orientation of the screw blocks and the communication of the threaded rod therewith which enables the raising and lowering of the stool when the cross bars rotate about their pivot points. The threaded actuating rod is influenced by a drive train driven by an electric motor. In the event that the motor fails to operate, that is, fails to actuate the rod, the step stool is provided with a hand crank which permits a user to raise and lower the step stool manually. The motor and drive train rotates the threaded rod raising and lowering the step stool through the operation of a pair of switches. For hands-free and relatively effortless control of the step stool, the switches are disposed beneath an anti-slip mat positioned on the upper surface of the top section. Fastened to each end of the stool is a handle to assist in the transport of the stool form one location to another. Attached to the bottom surface of the lower section are anti-skid pads which reduce the risk of the pad moving inadvertently. Bushings may be applied to pivotal areas to reduce frictional wear. Further, pads may be interposed between the individual sections to prevent the sections from making direct contact with one another and thus, reduce the risk of frictional wear between the various sections.

Accordingly, it is a principal object of the invention to provide an adjustable step stool comprising a telescopic body which vertically expands and contracts through the actuation of inner structural elements.

It is another object of the invention to provide a telescopic body having a top section, a intermediate section, and a bottom section.

It is another object of the invention to provide inner structural elements which include a scissor assembly comprising front and rear, longitudinally extending cross bars, each connected at a pivot point; left and right, laterally extending screw blocks; knee brackets adjoining the cross bars and the knee brackets; and a threaded actuating rod communicating with screw blocks.

It is another object of the invention to provide a step stool wherein when the rod is rotated, the screw blocks either converge or diverge from one another acting on the knee brackets which, in turn, cause the cross bars to rotate about their pivot points.

It is another object of the invention to provide a step stool wherein the one side of each cross bar engages with a roller assembly which permits longitudinal movement of the cross bars and wherein an opposite side of each cross bar is pivotally connected to a fixed pivot point.

It is another object of the invention to provide a step stool wherein the engagement of the cross bars with the roller assemblies and the fixed blocks as well as the orientation of the screw blocks and the communication of the threaded rod therewith enables the elevation and lowering of the stool to take place.

It is another object of the invention to provide a step stool wherein the actuating rod is influenced by a drive train driven by an electric motor.

It is another object of the invention to provide a step stool having a hand crank wherein in the event that the motor fails to actuate the rod, the hand crank permits a user to raise and lower the step stool manually.

It is another object of the invention to provide a step stool having a motor which is made operable to raise and lower the step stool through a pair of control switches.

It is another object of the invention to provide a step stool rendering hands-free and relatively effortless control of the elevation and lowering thereof accomplished through the positioning of the control switches on the upper surface of the step stool.

It is another object of the invention to provide step stool having handles fastened to each end of thereof to assist in the transport of the stool from one location to another.

It is still another object of the invention to provide a step stool having anti-skid pads attached to the bottom surface thereof which reduce the risk of the pad moving inadvertently.

It is further an object of the invention to provide a step stool having pads and bushings which are interposed between individual interacting sections and pivotal parts and which prevent the sections and pivotal parts from making direct contact with one another and thus, reduce the risk of frictional wear between the various sections and parts.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
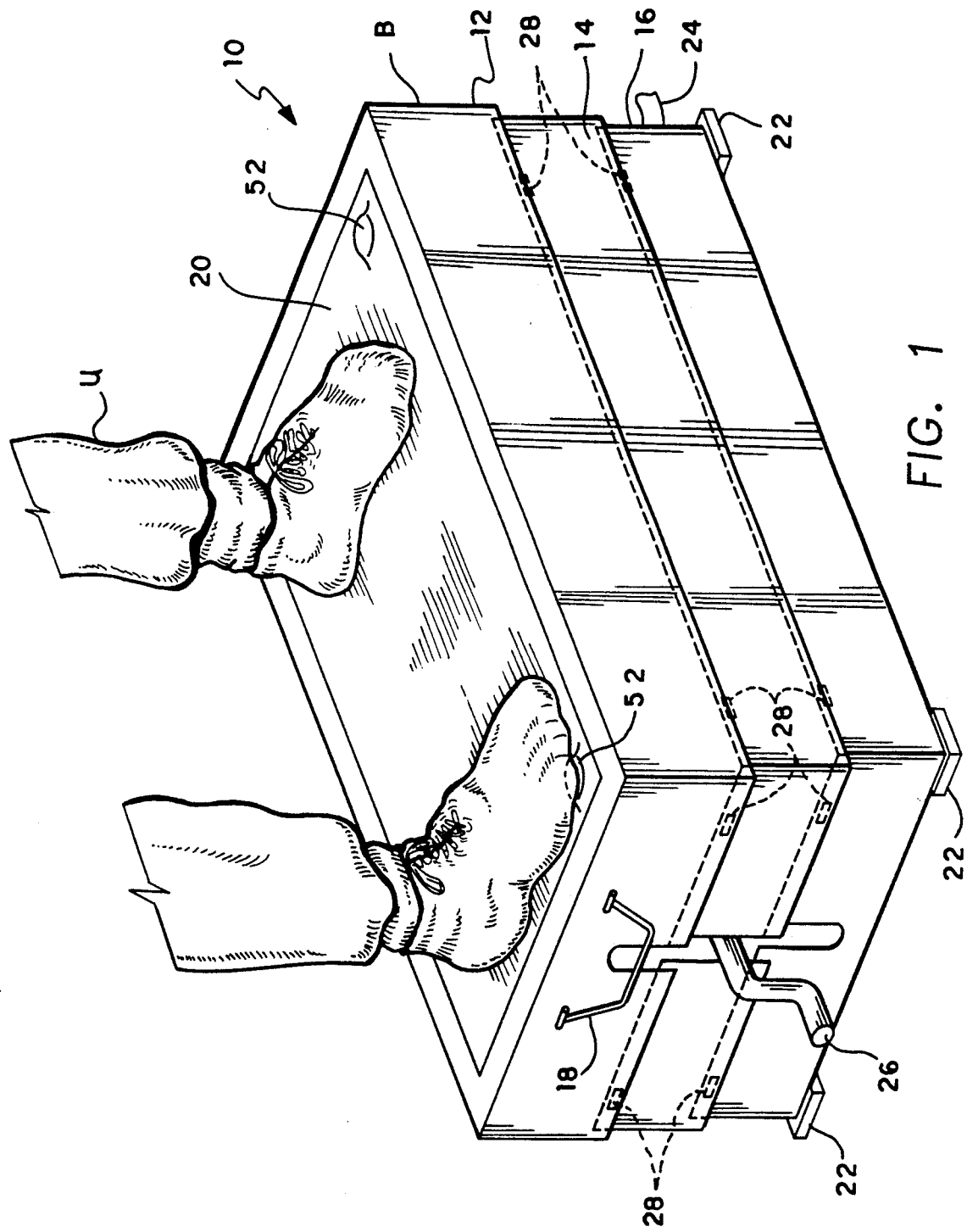
FIG. 1 is an environmental perspective view of the adjustable step stool.

The present invention, as shown in FIG. 1, is an adjustable step stool 10. The step stool 10 comprises an expandable or telescopic body B having plurality of stages. FIG. 1 shows the stool 10 having three stages, namely a top section 12, a intermediate section 14, and a bottom section 16, but the stool 10 can be configured of any number of stages or sections and is not limited to the three sections 12,14,16 shown. Shown in the broken line are pads 28, preferably fabricated of PTFE, interposed between the top section 12 and the intermediate section 14 as well as between the intermediate section 14 and the bottom section 16. These pads 28 prevent the individual sections 12,14,16 from communicating directly with one another. The top section 12 has an upper surface including an anti-slip mat 20 resting thereon. The top section 12 may be provided with a bordering edge surrounding the mat 20; that is to say, a recess may be provided for the receipt of the mat 20, whereby the upper surface may be flush. A pair of switches S1,S2 are provided to respectively elevate or lower the stool 10. These switches S1,S2 are located along the upper surface of the top section 12 and are oriented to be conveniently accessible through the mat 20. This accessibility allows the user U to adjust the height of stool 10 with virtually no effort involved. The bottom section 16 of the telescopic body B is provided with anti-slip pads or feet 22 which assist in maintaining the stool 10 in a stationary position, thus reducing the risk of injury caused by to an inadvertent shifting of the stool 10. The stool is raised and lowered via inner structural elements (shown in FIG. 2) located interiorly of the telescopic body B. The inner structural elements are preferably actuated by means of a series of electromechanical components (shown in FIG. 2) powered by a power source (not shown), the power being delivered from the power source to the series of electromechanical components through the use of a power cord 24. In the event that the electromechanical components fail to actuate the inner structural elements, a hand crank 26 is provided to allow the user U to manually elevate and lower the stool 10. The stool 10 further includes right and left handles 18 (right handle not shown) which permit the stool 10 to be picked up and transported from one location to another.

Figure 2:
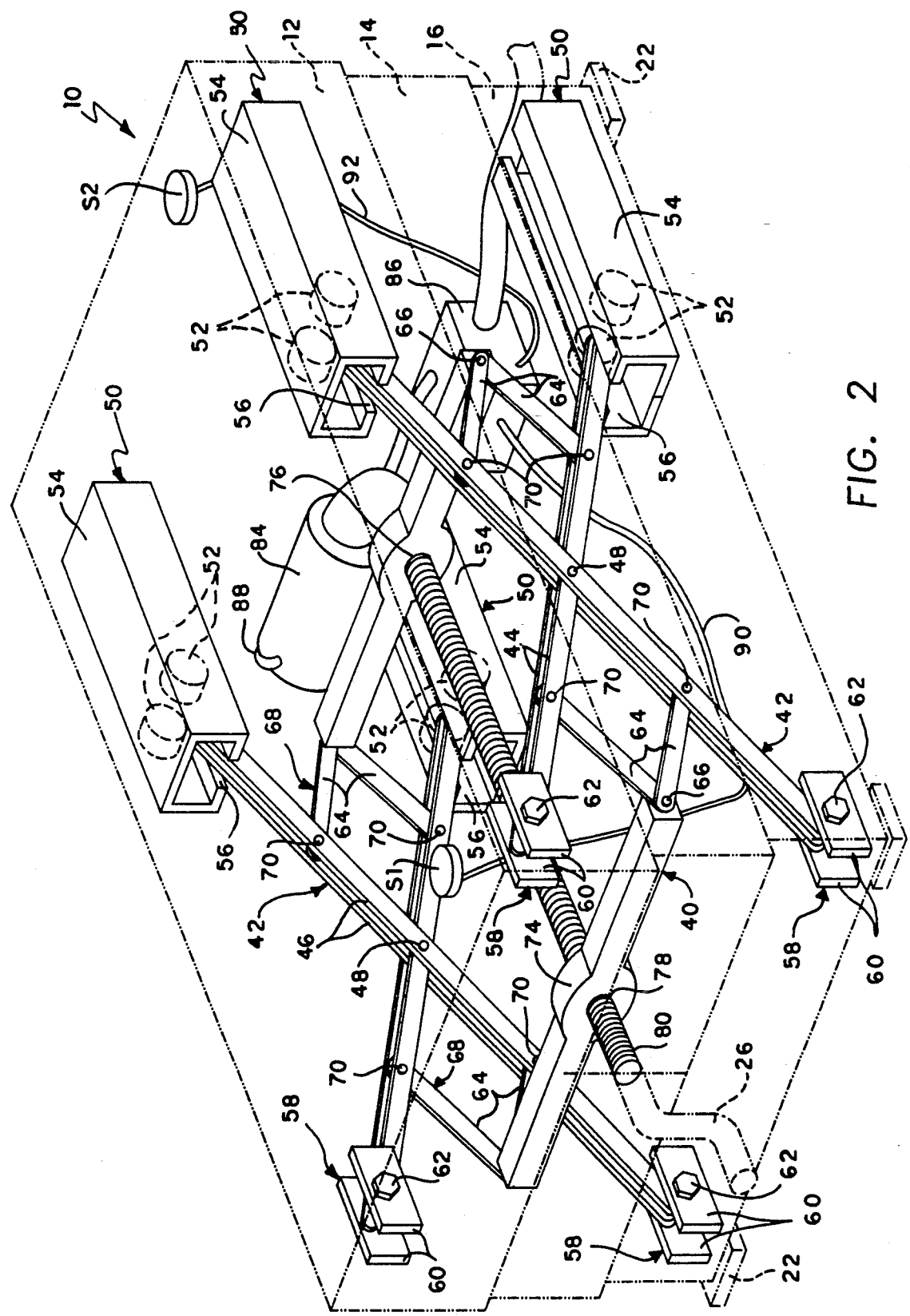
FIG. 2 is a perspective detail view of the adjustable step stool showing the inner structural elements and showing the telescopic body in broken lines.

FIG. 2 shows the inner structural elements disposed interiorly of the telescopic body B. The inner structural elements are comprising a scissor assembly 40 and a series of electromechanical components. The scissor assembly 40 includes both front and rear pivotal cross bars 42. Each cross bar 42 is fabricated of a first pair of elongated spaced apart beams 44 centrally and pivotally connected to a second pair of elongated spaced apart beams 46 by a centrally disposed pivot point 48. The spacing provided between each pair of beams 44,46 is produced by orienting of one of the beams 44 forming the first pair between the two beams 46 forming the second pair and by orienting of one of the beams 46 forming the second pair between the two beams 44 forming the first pair. This interconnection of beams 44,46 yields a front and rear X-shaped configuration, each having both upper and lower, left and right ends. The upper and lower right ends of these front and rear X-shaped configurations each engage with respective upper and lower, front and rear roller assemblies 50. Each roller assembly 50 is comprised of at least one roller 52 engagable with a fixed longitudinally disposed guide channel 54. The channels 54, shown in FIG. 2, are each configured of a hollow, rectangular member having a longitudinal slot 56 to permit the passage of a respective end of a beam 44,46. Also shown in FIG. 2 are a pair of rollers 52 being rotatably attached to each of the upper and lower, right ends of the front and rear X-shaped configurations. These rollers 52 are engaged with and are permitted to travel longitudinally interiorly of the respective channels 54. As the X-shaped configuration expands and contracts vertically, the rollers 52 travel longitudinally within a respective channel 54 thereof and a portion of each beam 44,46 proximate the respective rollers 52 travels longitudinally within and along a relative slot 56 thereof. The upper and lower left ends of the front and rear X-shaped configurations each engage with respective upper and lower, front and rear fixed pivots assemblies 58. Each pivot assembly 58 is comprised of at least one elongated rectangular plate 60 and a pivot pin 62, such as the bolt shown, engagable with the rectangular plate 60. The pair of rectangular plates 60, shown in FIG. 2, are each disposed in a vertical plane and thus, are arranged parallel to the attitude of the beams 44,46. The pin 62 is purposed to pivotally fix the respective upper and lower, left ends of the relative pair of beams 44,46. As the X-shaped configuration expands and contracts vertically, the left ends of the beams 44,46 pivot on the plates 60. A first and second elongated bar 64 of equal length, each have ends which are joined together by a pivot pin 66 to form a knee bracket 68. The knee brackets 68 enhance the stability, reduce the stress imposed on the pivotal areas and thus, further reduce the wear between the moving elements. The first and second elongated bars 64 each have ends opposite the adjoining ends, one of these ends opposite the adjoining ends being pivotally connected to one beam 44 and the other being pivotally connected to the other beams 46. These connections are each accomplished via a pivot pin 70 and are located equidistantly between the central disposed pivot point 48 and the roller assembly 50 and are located equidistantly between the central disposed pivot point 48 and the fixed pivots 58. The pivot pin 66 not only pivotally connects the two elongated bars 64 to one another, but also pivotally links right and left screw blocks 72,74 to the elongated bars 64. The right and left screw blocks 72,74 are laterally interposed between the front and rear pivotal cross bars 42, joining respective front and rear knee brackets 68 which, in turn, join front and rear cross bars 42. The placement of the roller assemblies 50, the fixed pivots 58, and the knee brackets 68 as well as the engagement of the various foregoing inner structural elements in combination maintain the front and rear cross bars 42 in a parallel relation with one another. The right and left screw blocks 72,74 each include an aperture 76,78. The aperture in the left screw block 78 is threaded whereas the aperture in the right screw block 76 is not threaded. These apertures 76,78 are axially aligned with one another and adapted to commonly receive a single, elongated threaded actuating rod 80. The rod 80 simply passes through the unthreaded right screw block 72 and then threadably engages with the female threaded aperture 78. By rotating or turning the threaded rod 80 clockwise, the right and left screw blocks 72,74 converge toward one another, thus vertically expanding the front and rear cross bars 42. Conversely, by rotating the threaded rod 80 counter clockwise, the right and left screw blocks 72,74 diverge causing the front and rear cross bars 42 to vertically contract. The expanding and contracting of the cross bars 42 causes the raising and the lowering of the telescopic body B. Keep in mind that all of the aforementioned pivot points preferably include bushings which reduce the frictional wear of the pivotal elements.

The series of electromechanical components includes a reversible electrical motor 84, an electrical control box 86 and a pair of switches S1,S2, all tied together with a plurality of conductors 88,90,92, one conductor 88 supplying power to the motor 84, one conductor 90 tying the raising switch S1 to the control box 86, and one conductor 92 tying the lowering switch S2 to the control box 86. The control box 86 may include an arrangement of control devices which are capable of controlling the polarity of the current flowing to the motor 84, thus control the direction in which the motor 84 operates. The control box may also include a rechargeable power source which may supply current to operate the motor 84 when the step stool 10 is in use and which may be charged when not in use. Current is permitted to flow when the switches S1,S2 are depressed. By depressing the switches S1,S2, the control devices are activated, thus closing a current loop and actuating the motor 84. The switches S1,S2 are concealed beneath the mat 20 (shown in FIG. 1). Though the switches S1,S2 are concealed, the switches S1,S2 are accessible through the mat 20, thus enabling the user U (shown in FIG. 1) to change the state of the switches S1,S2 with his or her feet. A single switch could be employed to limit the switch S1,S2 actuation. Such a device could include a timer mechanism that requires the state of the switch S1,S2 to be change a certain number of times within a preestablished time frame or a time delay mechanism which would not activate the motor 84 immediately after the switch was depressed. When the motor 84 is actuated, the threaded rod 80 is rotated either clockwise or counter clockwise. Driving the rod 80 is accomplished through the interconnection of the motor 84 with the rod 80. This interconnection is established through some conventional method. For safety and operational purposes, a cover is provide to conceal and protect connecting elements which connect the motor 84 and the rod 80. The power is supply to the control box 86 through the employment of a power cord 24.

It is to be understood that the present invention is not limited to the sole embodiment described above, but encompasses any and all embodiments within the scope of the following claims.

I claim:
1. An adjustable step stool comprising:
 a) a vertically expandable and contractible body;
 b) a scissor assembly disposed interiorly of said body, said scissor assembly being vertically expandable and contractible, wherein said scissor assembly further includes:
  (1) a pair of laterally extending screw blocks;
  (2) a pair of longitudinally extending cross bars;
  (3) a plurality of knee brackets, said screw blocks and said cross bars being pivotally joined together by said knee brackets in such a manner that said screw blocks are held in a parallel spaced apart configuration relative to one another and said cross bars are held in a parallel spaced apart configuration relative to one another; and
  (4) a threaded actuating rod, said threaded actuating rod being journaled through a one of said knee brackets and being threaded through another one of said screw blocks whereby,
   when said rod is rotated in a one direction, said screw blocks converge, causing said cross bars to expand vertically and, in turn, causing said step stool to lower;

c) a motor engagable with said scissor assembly and purposed for driving said scissor assembly to an expanded and contracted posture;

d) means for defining a switch located proximate an upper surface of said body; and e) a hand crank connected to said scissor assembly, whereby said hand crank may rotate in a selective direction to elevate and lower said step stool.

2. The step stool according to claim 1, further includes means to reduce a risk of an inadvertently raising or lowering said step stool.

3. The step stool according to claim 1, further includes a control box containing a plurality of control devices to facilitate in selectively controlling said motor.

4. The step stool according to claim 1, further includes means to impress potential across said motor.

5. The step stool according to claim 1, further includes a handle located exteriorly of said body, said handle facilitates in the transport of said step stool.

6. The step stool according to claim 1, further includes an anti-slip mat positioned on said upper surface of said body, said mat overlaps said switch in such a manner that said mat lays substantially flush and said switch is controllable through said mat.

7. The step stool according to claim 1, further includes anti-slip feet juxtaposed a bottom surface of said body whereby said feet are interposed between said bottom surface and a supporting surface sustaining said step stool, thus preventing said step stool from inadvertently slipping and, in turn, reducing risk of injury being sustained by the user.

8. The step stool according to claim 1, wherein said means defining a switch includes a first and second switch, a one said switches to facilitate in elevating said step stool and another one said switches to facilitate in lowering said step stool.

9. An adjustable step stool comprising:

a) a telescopic body;

b) a scissor assembly contained within said telescopic body, said scissor assembly including:
 1) front and rear, longitudinally extending cross bars, each having a centrally disposed pivot point;
 2) a plurality of roller assemblies, each being respectively engagable with corresponding right ends of each of said cross bars;
 3) a plurality of fixed pivots, each being respectively pivotally connected to corresponding left ends of each of said cross bars;
 4) left and right, laterally extending screw blocks;
 5) a threaded actuating rod journaled though a one of said screw blocks and threadably engaging with another one of said screw blocks whereby when said rod is rotated in a one selected direction, said screw blocks converge and when said rod is rotated in another one selected direction, said screw blocks diverge; and
 6) knee brackets, each having a centrally disposed pivot point and ends opposite said centrally disposed pivot point, each of said screw blocks being respectively pivotally connected to said knee bracket proximate said pivot point and each of said opposite ends of each of said knee brackets being respectively pivotally connected to a corresponding point on said cross bar whereby when said screw blocks converge, said cross bars expand vertically causing said step stool to raise and when said screw blocks diverse, said cross bars contract vertically causing said step stool to lower; and c) a series of electromechanical components contained within said telescopic body including:
 1) means defining a switch disposed adjacent to and accessible from a upper surface of said telescopic body, whereby a state of said switch can be changed by a foot of a user standing on said upper surface of said step stool;
 2) a motor engagable with and purposed for driving said actuating rod;
 3) a control box containing a plurality of control devices for selectively controlling said motor;
 4) a plurality of conductors to facilitate in interconnecting said switch with said control box and for interconnecting said control box with said motor; and
 5) means to impress potential across said motor, whereby the user may be positioned on said step stool adjacent said switch such that the state of said switch may be easily changed to selectively actuate said control devices and in turn, energize said motor drive said rod and thus, raise or lower said step stool.

10. The step stool according to claim 9, including a first and second switch forming said means defining a switch whereby the state of a one said switch may be changed to elevate said step stool and whereby the state of another one said switch may be changed to lower said step stool.

11. The step stool according to claim 9, wherein said control box includes a portable rechargeable power source which enables the step stool to be used when and in areas where other power sources are not available.

12. The step stool according to claim 9, wherein said telescopic body includes a top section, an intermediate section, and a bottom section.

13. The step stool according to claim 12, further including padding interposed between said top section and said intermediate section as well as between said intermediate section and said bottom section, whereby said padding reduces a frictional wear sustained by each of said sections by preventing said sections from communicating directly with one another.

14. The stepping stool according to claim 11, further including bushings applied to said plurality of fixed pivots of said scissor assembly to reduce wear.

15. The step stool according to claim 9, further including a handle located exteriorly of said telescopic body, said handles facilitates in the transport of said step stool.

16. The step stool according to claim 9, further including an anti-slip mat positioned on said upper surface of said step stool, said mat covers said switch in such a manner that said mat is substantially flush and in such a manner so as to enable the state of said switch to be changed.

17. The step stool according to claim 9, further including anti-slip feet juxtaposed a bottom surface of said step stool whereby said feet are interposed between said bottom surface and a supporting surface sustaining said step stool preventing said step stool from inadvertently slipping and thus, reducing a risk of injury being sustained by the user.

18. The step stool according to claim 9, further including a hand crank connected to said actuating rod whereby said hand crank may rotated in a selective direction to elevate and lower said step stool.

* * * * *